United States Patent
Kostylev et al.

[19]
[11] Patent Number: 6,159,162
[45] Date of Patent: Dec. 12, 2000

[54] BIOPSY APPARATUS

[75] Inventors: Alexander N. Kostylev; Constantine V. Novikov, both of St. Petersburg, Russian Federation; Leon L. Pesotchinsky, Los Altos Hills, Calif.

[73] Assignee: LSVP International, Inc., Los Altos, Calif.

[21] Appl. No.: 09/305,685

[22] Filed: May 4, 1999

Related U.S. Application Data

[60] Provisional application No. 60/084,005, May 4, 1998.

[51] Int. Cl.$^7$ ...................................................... A61B 5/00
[52] U.S. Cl. ............................................................ 600/564
[58] Field of Search ................................... 600/564–567; 606/205, 207, 208

[56] References Cited

U.S. PATENT DOCUMENTS

| | | | |
|---|---|---|---|
| 4,815,476 | 3/1989 | Clossick | 128/751 |
| 4,817,630 | 4/1989 | Schintgen et al. | 128/751 |
| 4,887,612 | 12/1989 | Esser et al. | 128/751 |
| 5,097,728 | 3/1992 | Cox et al. | 76/119 |
| 5,172,700 | 12/1992 | Benicini et al. | 128/751 |
| 5,373,854 | 12/1994 | Kolozsi | 128/749 |
| 5,395,369 | 3/1995 | McBrayer et al. | 600/564 |
| 5,419,220 | 5/1995 | Cox | 76/104.1 |
| 5,535,754 | 7/1996 | Doherty | 128/751 |
| 6,010,523 | 1/2000 | Sabin et al. | 600/564 |

*Primary Examiner*—Max Hindenburg
*Attorney, Agent, or Firm*—Carol D. Titus; James J. Leary

[57] ABSTRACT

An endoscopic instrument having one or two moving jaws. The jaws are pivotally attached to a housing and actuated by a central control wire attached to an actuation mechanism. Preferably, a portion of the housing forms a pin for each jaw around which the jaw pivots. The actuation mechanism moves back and forth along the body of the instrument. Engagement projections extend from opposing sides of the body of the actuation mechanism. The engagement projections engage openings in the jaws. As the actuation mechanism is moved toward the distal end of the instrument, the jaws are moved toward an open position. As the actuation mechanism is moved toward the proximal end of the instrument, the jaws are moved toward a closed position. Optionally, the jaws maybe configured to open to a predetermined, maximum angle.

33 Claims, 5 Drawing Sheets

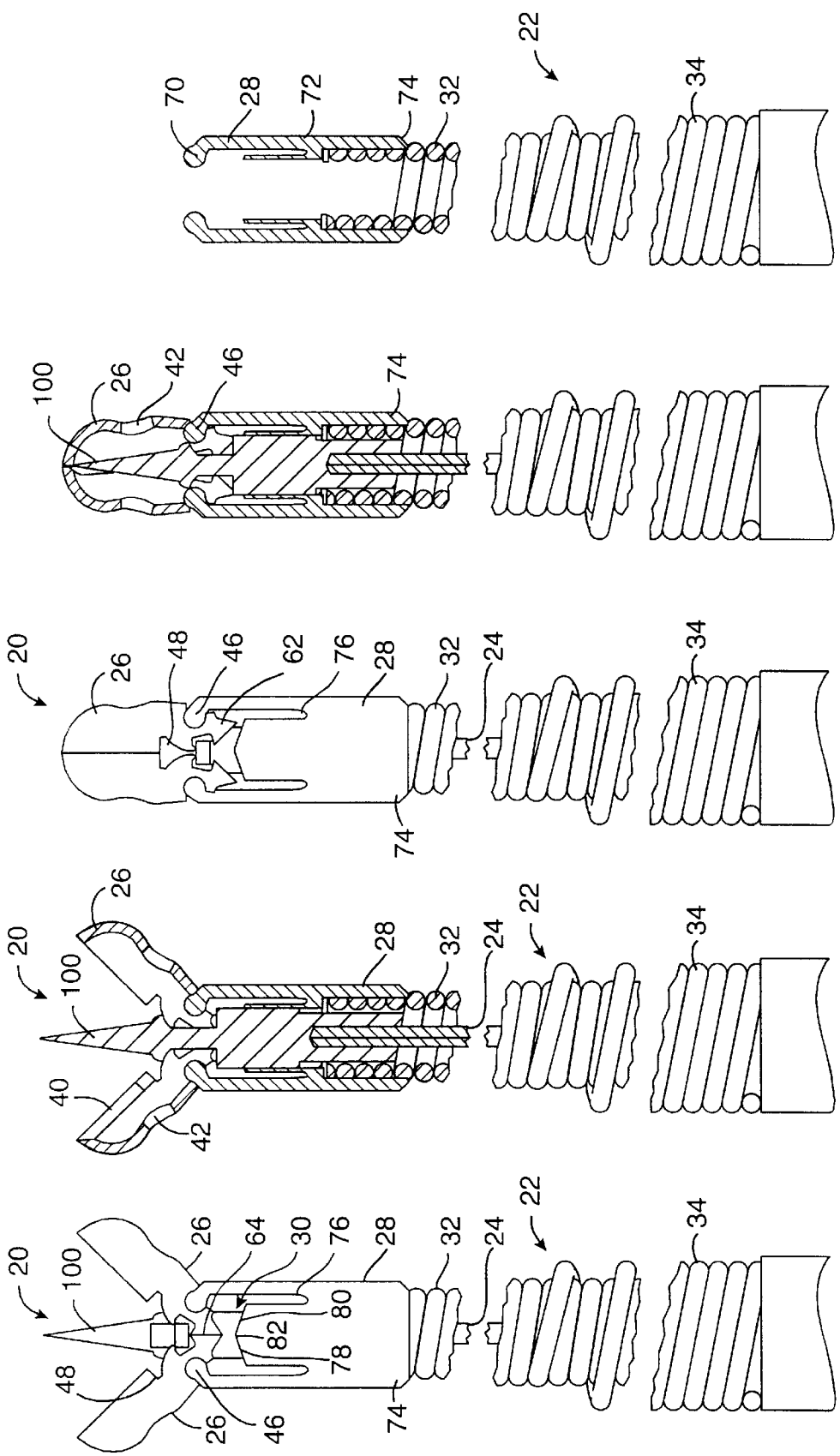

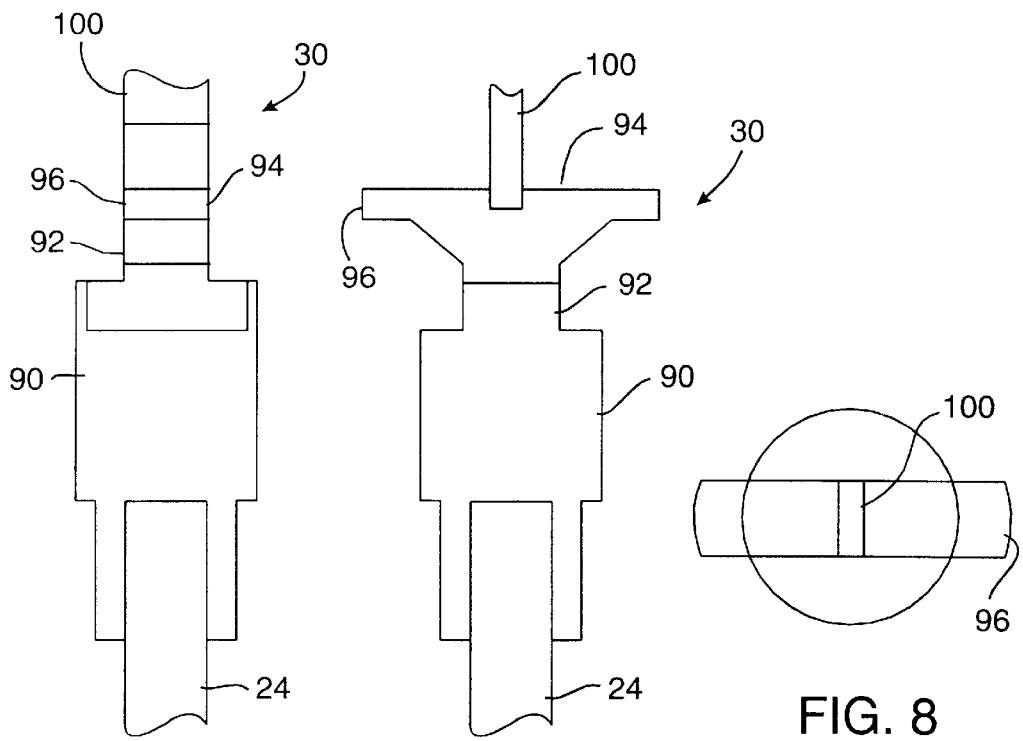
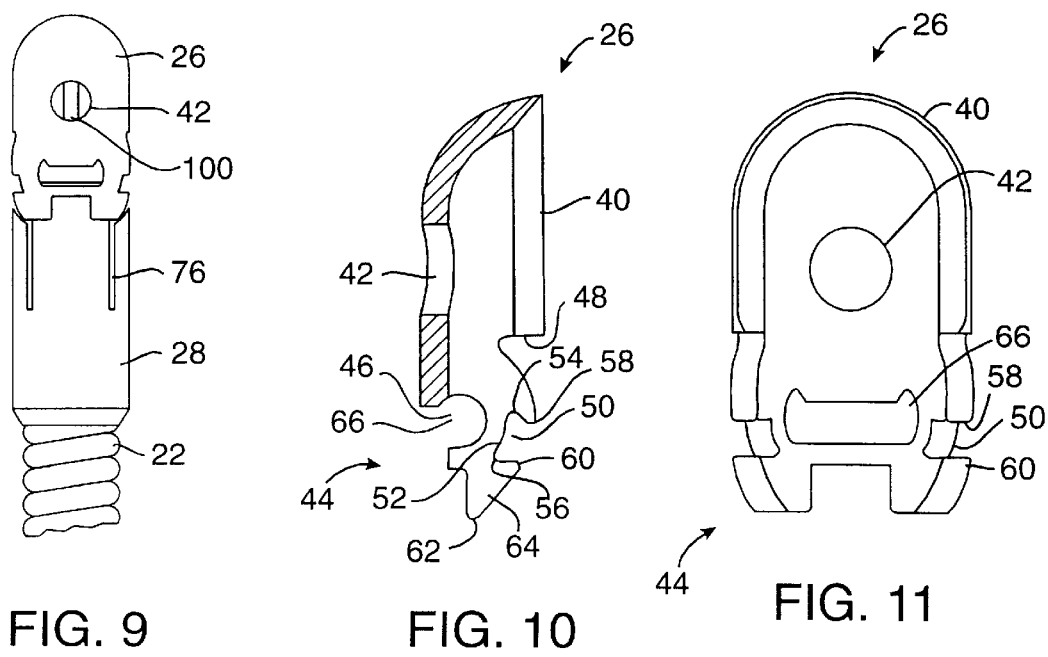

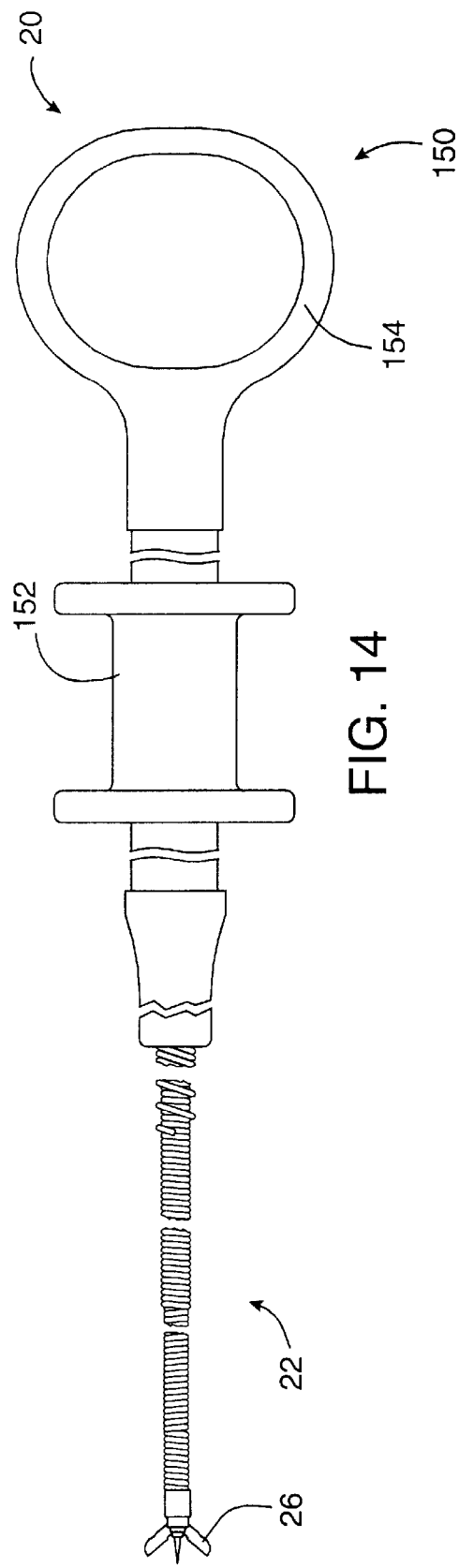
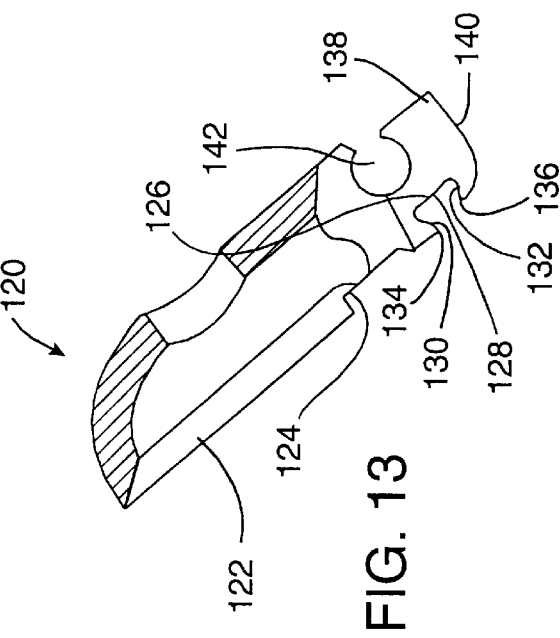
FIG. 14
FIG. 13

BIOPSY APPARATUS

CROSS REFERENCE TO OTHER APPLICATIONS

This application claims the benefit of U.S. Provisional Patent Application No. 60/084,005, filed May 4, 1998, which is hereby incorporated by reference in its entirety.

FIELD OF THE INVENTION

The present invention relates to medical instruments. More particularly, it relates to an endoscopic instrument that may be used as biopsy forceps, graspers, etc.

BACKGROUND OF THE INVENTION

Over time, a variety of endoscopic biopsy forceps, graspers, and other related apparatuses have been developed to take samples of tissue or grasp and remove material during endoscopic procedures. Normally, the forceps, which are adapted to cut and remove body tissue for examination, are inserted together with an endoscope deep into a body cavity being examined. The forceps conventionally used in such procedures utilize complex arrangements of linkage assemblies or cam type devices for articulating the jaws of the forceps. As such instruments are of small size, such complexity results in complex machining and manufacturing procedures which greatly increase the cost of such instruments. The multiple connections also increase the amount of play, which may increase the distortion of the movement of the jaws of the device. Thus, present biopsy devices are generally very expensive and, the jaw actuating mechanisms are complex and may be inaccurate.

The small size and number of the linkages and hinge pins also decrease the durability of the biopsy forceps and make them vulnerably to breakage. This is an important consideration, especially when working within a patient where retrieval of a dissociated part may be difficult or dangerous to the patient. Large numbers of small linkages and hinges also increase the cost and difficulty of manufacturing and assembly.

The combination of jaws, linkages, and outer housing results in an instrument jaw/housing assembly having a significant rigid length. This rigidity associated with the instrument increases the difficulty of navigation through the bent channel of the endoscope, as well as increasing the potential for damage of the endoscope instrument channel through which the device is passed to obtain a tissue sample. A single endoscope may be used for many endoscopic procedures, and, in some cases an endoscopic biopsy procedure requires multiple insertions and removals of the device. Each insertion or removal of the biopsy instrument through the narrow channel in the endoscope can cause potential damage to the channel of the endoscope or to the biopsy instrument itself. This is especially problematic in cases where a tortuous passage leads to the cavity from which the sample is obtained.

Further damage to the endoscope instrument channel may be caused by a link or a member of the forceps which protrudes from the perimeter of the rest of the forceps. This problem may arise if the forceps are unable to close completely or if a portion of the mechanism jams, or even if the mechanism merely has excess play. When the forceps are inserted or removed from the endoscope under these conditions, the exposed link or member may scrape, scratch or otherwise damage the channel.

Since many current biopsy devices are intended for multiple use, damage to the endoscope or biopsy device itself is even less desirable. Furthermore, in conventional biopsy forceps, the intended multiple use of the instrument requires extensive cleaning and sterilizing procedures to be performed to comply with medical standards and use of the instruments. When used multiple times, a biopsy instrument must be sterilized between uses by immersing a contaminated instrument in a suitable chemical sterilizing solution, subjecting the apparatus to sterilization in an autoclave, or some other sterilization procedure. The sterilization and cleaning procedures will often decrease the performance or useful life span of the instrument, thereby magnifying the problem created by the complexity of manufacture and many parts which quickly wear. Further, some devices which are intended only for single use still incorporate complex linkage or cam type devices for proper movement of the biopsy jaws. This greatly inhibits their use as the costs associated with such instruments are normally still very high.

Other deficiencies of the prior art endoscopic biopsy forceps are found in activation of the biopsy jaws for opening and closing of the jaws. The complexity and many moving parts of prior art devices cause the jaws to misalign when the jaws are actuated. This is also a problem with devices which utilize a living hinge. A living hinge operates by using the flexibility and deformation of the material of the hinge to allow the jaws to move. However, the same flexibility allows the jaws to twist which means that the cutting edges of the jaws may not meet properly and the sample is not removed cleanly from the rest of the organ. In extreme cases, the forceps may fail entirely and require that a new instrument be used and/or a lost piece of the instrument be retrieved from the patient.

SUMMARY OF THE INVENTION

The present invention provides a biopsy apparatus, in the form of forceps, graspers or other similar devices, for taking a tissue sample having one or two moving sections. When properly used, the movement of the jaws of the forceps is stable and the jaws are unlikely to misalign due to damage or deformation of the device. The instabilities created by the multiple links and linkage assemblies of the prior art is reduced by elimination of many of the linkages and particularly the hinge pin as a separate member. The jaws and the housing may be formed of a generally rigid material, with a portion of the housing itself acting as a pin about which the jaws rotate. The present configuration allows only minimal play thereby increasing the accuracy of the alignment of the jaws and decreasing the difficulty of taking a sample, as well as decreasing the risk of damage to the sample taken, the endoscope, and the forceps. This is an important advantage over the prior art, which may allow significant deformation of the linkages causing the jaws to misalign. Further, since many of the linkages, pins and other members are eliminated, the connections may be more robust and therefore be even less vulnerable to deformation while still allowing a smaller overall size for the biopsy forceps.

Many of the prior art devices, due to the many linkages and linkage assemblies require a relatively long housing, which is disadvantageous when performing endoscopic procedures, especially when the path to the tissue sample site is tortuous, convoluted, narrow, or a combination thereof. The longer the rigid portion of the housing, the increased likelihood that the endoscope or the biopsy forceps will be damaged during the procedure or that the user will be unable to properly place the forceps to take the sample. The present invention allows a significantly shorter housing, since the range of motion of the actuation member is a minimal addition to the length of the jaws. The rigid portion of the device is made up of the jaws and the housing. The overall length of the rigid portion in the prior art is frequently more than triple or quadruple the length of the jaws, thereby forming a significant rigid length which must be feed gently through the endoscope's channel.

Further, some prior art devices use significant portions of the internal cavity of the jaws for the actuation mechanism, thereby decreasing the size of the sample taken or increasing the size of the jaws. In the present invention, the jaws of the device are generally unencumbered, so virtually the entire length of the jaws may be used for the tissue sample.

Many of the prior art devices also require that additional space be available surrounding the rigid housing during operation of the forceps to allow for the multiple linkages to move beyond the boundary of the rigid housing or sleeve. The present invention operates completely within the housing. The only portion of the device which moves out beyond its initial perimeter is the jaws as they open to obtain a sample.

In keeping with the foregoing discussion, the present invention takes the form of a jawed endoscopic instrument which has one or two moving jaws. The jaws are pivotally attached to a housing and actuated by a central control wire attached to an actuation mechanism. Preferably, a portion of the housing forms a pin for each jaw around which the jaw pivots. The actuation mechanism moves back and forth along the body of the instrument. Engagement projections extend from opposing sides of the body of the actuation mechanism. The engagement projections engage openings in the jaws. As the actuation mechanism is moved toward the distal end of the instrument, the jaws are moved toward an open position. As the actuation mechanism is moved toward the proximal end of the instrument, the jaws are moved toward a closed position. Optionally, the jaws maybe configured to open to a predetermined, maximum angle.

BRIEF DESCRIPTION OF THE DRAWINGS

FIG. 1 is a side view of the endoscopic biopsy forceps in the open position.

FIG. 2 is a side cross-sectional view of the endoscopic biopsy forceps in the open position.

FIG. 3 is a side view of the endoscopic biopsy forceps in the closed position.

FIG. 4 is a side cross-sectional view of the endoscopic biopsy forceps in the closed position.

FIG. 5 is a side cross-sectional view of the housing and sheath of the endoscopic biopsy forceps.

FIG. 6 is a side view of the actuation mechanism of the endoscopic biopsy forceps.

FIG. 7 is a front view of the actuation mechanism of the endoscopic biopsy forceps.

FIG. 8 is a top view of the actuation mechanism of the endoscopic biopsy forceps.

FIG. 9 is a front view of the endoscopic biopsy forceps.

FIG. 10 is a side cross-sectional view of one of the jaws of the forceps.

FIG. 11 is an internal view of one of the jaws of the forceps.

FIG. 13 is a side view of an alternate jaw.

FIG. 14 is a side view of the instrument.

DETAILED DESCRIPTION

Figure 15:
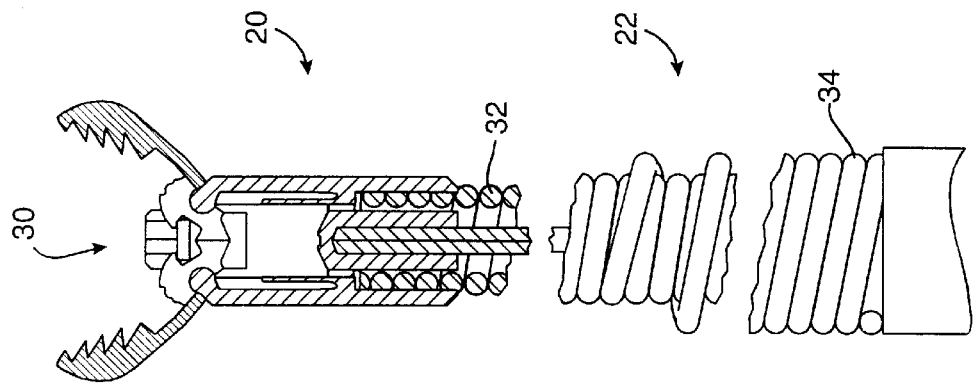
FIG. 15 is a side cross-sectional view of grasping forceps.

Although the present invention may take other forms such as graspers, the device shown in FIGS. 1–11 are biopsy forceps 20 for use in endoscopy to take tissue specimens from the body. The biopsy forceps 20 includes a flexible sheath 22, such as a flexible polymeric tubing, coiled steel or the like, having a first end from which control of the forceps 20 is effected by the user. A suitable operating mechanism for actuating the forceps is provided at the first end of the sheath 22 which is connected to a control wire 24. The control wire 24 is longitudinally movable within the sheath 22, and the suitable- operating mechanism or means will control movement of the control wire 24 therethrough. The device further includes a pair of biopsy jaws 26 connected to a housing 28 which is fixedly attached to the second end of the sheath 22. The biopsy jaws 26 are operatively connected to the control wire 24 by an actuator 30, which will be more fully described herein. At least one of the jaws 26 is moveable between open and closed positions with respect to the other of the jaws 26. However, in the embodiment shown, both jaws 26 are moveable between open and closed positions.

Although many other configurations are envisioned, in an exemplary embodiment the sheath 22 would be formed from two welded sections of coil 32, 34. The distal portion of the sheath 22 is preferably more flexible than the proximal portion. The added flexibility may be created by tapering the coil 34 by grinding. In another embodiment (shown in FIG. 14), the sheath is formed of three sections which are laser welded together. Although other sizes may be used, the present embodiment uses three sections which are preferably formed of coils which are 0.4, 0.5 and 0.6 mm. in diameter. The largest section is located at the proximal end and the smallest section is formed at the distal end. This configuration allows for the maximum flexibility at the distal end where it is most useful. One or more of the sections of coil may be coated with teflon. The teflon coating reduces friction use. Teflon coating also allows fitting the instrument with electrodes to form electrocautery or hot instruments. The electrocautery instruments can take a sample of tissue and electrocauterize the bleeding spot. If electrocautery is desired, an appropriate handle having an electrode should be chosen.

The control wire 24 is preferably a multi-strand cable, such as a 7 or 13 strand cable, but may also be solid, coiled, etc., depending on the requirements or qualities desired.

The length of the forceps 20 will vary greatly depending on the intended use. Standard forceps 20 are currently designed in the range of 20–260 centimeters. However, the present invention may be longer or shorter than this range if desired.

The forceps 20 may also be designed for other uses such as laparoscopic surgery or any other device which requires accurate movement of jaws 26 between open and closed positions, and may therefore be made in a variety of diameters from less than a centimeter to a meter or more depending on the application. As biopsy forceps 20, current standard diameters include a wide range of instrument diameters between 1.0 and 10.0 mm. Bother larger and smaller sizes may be created depending on the needs of the user. The operating mechanism is preferably formed into a handle comfortable for the user to hold and actuate. A sliding trigger may take the form of a spool or two-finger pull which slides along a stem. A thumb ring may be formed into or attached to the end of the stem. The thumb ring has a hole through which a thumb or finger may rest to aid in moving the sliding trigger by providing opposing pressure. If preferred, a scissor-type, pistol grip or other style handle may also be used.

The biopsy device 20 shown in the figures has two generally cup-shaped jaws 26. One or both of the jaws 26 preferably has a perimeter which tapers to form a cutting edge 40. If only one of the jaws 26 is moveable and only one has a cutting edge 40, the cutting edge 40 would optimally be located on the moving jaw 26. When moved into the closed position, the jaws 26 cut through the tissue and meet to remove a tissue sample from an organ and contain the sample during the removal process. An optional hole 42 may extend through the wall of one or both of the jaws 26. The hole 42 allows fluid or other extraneous material to escape the jaws 26 as the jaws 26 close, thereby causing less trauma to the sample being removed from the patient. The base 44 of each moveable jaw 26 is configured to rotate about its own pivot point 46.

Moving around the jaw 26 clockwise beginning with the cutting edge 40, the configuration of the jaw 26 perimeter is as follows. Below the cutting edge 40 is an optional notch 48 in the edge of the jaw 26. In the figure shown, the notch 48 is generally triangular, however, the notch 48 may be other shapes if desired. The notch 48 provides a transition between the cutting edge 40 and thicker portion of the jaw 26. Below the notch 48 is an actuator engagement opening 50. The opening 50 is oblong with a convex-curved back wall 52, a rounded upper end 54, and a rounded lower end 56. An upper projection 58 extends down from the upper wall 54 of the opening 50, and a lower projection 60 extends up from the lower wall 56 of the opening 50. The base 44 of each jaw 26 may have a triangular projection 62 which extends downward from the jaw 26 to form a limit surface 64 to prevent over-rotation of the jaws 26. Above the triangular projection 62 is a generally circular opening 66. The opening 66 is preferably greater than 180 degrees in circumference; as shown, it is approximately 270 degrees. The opening 66 provides a connection with the housing 28 by containing a generally cylindrical portion 70 of the housing 28 which will be more fully described. the opposing side of the jaw 26 is preferably shaped the same.

The housing 28 is preferably a generally cylindrical body 72 through which the control wire 24 joins to the actuator 30. The base 74 of the housing 28 is connected to the second end of the sheath 22. The connection may be created by soldering, adhesive, crimping, threading, welding or other known connection methods. The pivot points 46, about which the jaws 26 rotate, are created by generally cylindrical portions 70 of the housing 28 which are located at or near the upper end of the housing 28 and preferably extend slightly inward from the side of the housing 28. When assembled, the cylindrical portions 70 of the housing 28 are situated within the generally circular openings 66 in the base sections 44 of each jaw 26, thereby creating a pivot about which each jaw 26 rotates. A plurality of slots 76 extend downward proximate the generally cylindrical portions 70. The slots 76 allow the housing 28 to expand slightly during the assembly process. Although more or less may be used, if four slots 76 are used, the cylindrical portions 70 extend between two opposing portions of the housing 28 as divided by the slots 76. The remaining two portions of the housing 28 are partially cut away to allow the triangular portions 62 of the base 44 of the jaws 26 to freely rotate. In the embodiment shown, the cut-away edge 78 has two slanted sections 80 which meet in a cusp 82 at the center. This configuration cuts away a minimal amount of the housing 28 to retain the stability of the housing 28. If preferred, the cut away section could be alternately shaped, or the cut-away could omitted entirely if the base 44 of the jaws 26 were configured differently.

In the particular configuration shown, movement of the jaws 26 is created by an actuator 30 which is directly connected to the control wire 24. A generally cylindrical base portion 90 is fixedly attached to the control wire 24. The connection may be created by soldering, adhesive, crimping, welding or other known connection methods. Extending from the top of the base portion 90 is a connecting stem 92. The top of the connecting stem 92 widens out into the actuation member 94, which has two engagement projections 96, one on each side. When assembled, each engagement projection 96 is located within the actuator engagement openings 50 of the jaws 26. The upper projection 58 of the opening 50 extends above an engagement projection 96 and may engage the upper surface of the engagement projection 96. The lower projection 60 of the jaw 26 extends below the engagement projection 96 and may engage the lower surface of the engagement projection 96. Therefore, when the actuator 30 is moved upward by pushing on the control wire 24, the top surfaces of the engagement projections 96 pushes the upper projections 58 upward, thereby rotating the jaws 26 apart. When the actuator 30 is moved downward by pulling on the control wire 24, the lower surface of the engagement projection 96 pulls the lower projections 60 downward, thereby rotating the jaws 26 together.

When the jaws 26 are in the fully open position, the inside edges 64 of the triangular portions 62 on the bases 44 of the jaws 26, if present, meet flush against one another and provide a limit stop to prevent the jaws 26 from opening beyond the desired amount. In the open position, a typical angle between the jaws 26 is in the range of 60 to 120 degrees, preferably from 75 to 105 degrees. However, the opening could be designed within a greater range, such as 15–180 or more, if desired. For example, if the desired opening is 90 degrees, then, in the closed position, the inside edge of the triangular portion 62 would be at 45 degrees. When the jaws 26 are opened to 90 degrees, the inside surfaces 64 meet and prevent further rotation of the jaws 26. The limit surfaces 64 may be formed on other shaped projections depending on the design requirements.

The device may optionally include a spike 100 attached to the upper surface of the actuation member 94. The spike 100 is used to facilitate the taking of tissue samples during use. Since the spike 100 is connected to the actuation mechanism 30, when the actuation mechanism is moved to close the jaws, the spike is moved farther into the jaw cavity. This motion acts to draw the sample into the jaws as the jaws are closed. If preferred, the spike 100 may be barbed to more securely retain and pull the sample gently into the forceps 20 while the jaws 26 are closing to cut away the sample.

Figure 12:
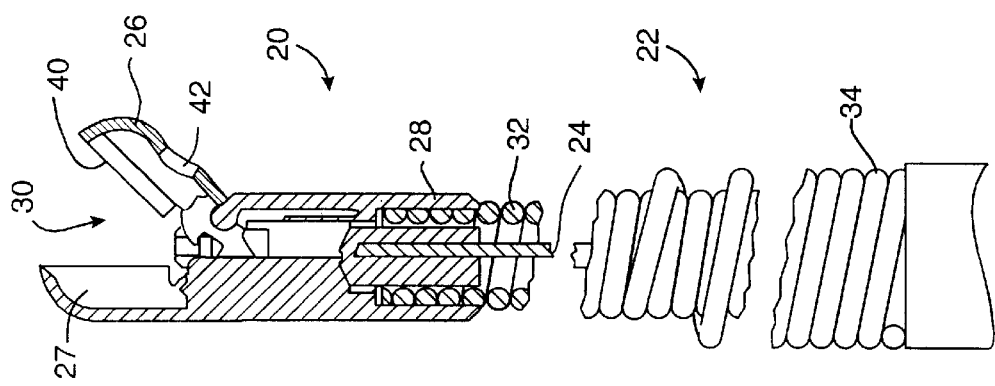
FIG. 12 is a side cross-sectional view of the endoscopic biopsy forceps having a single moving jaw.

If preferred, the forceps 20 may be formed with a single moveable jaw 26, as shown in FIG. 12, in which case, the actuation mechanism 30 would engage only one of the jaws 26. The other jaw 27 would be fixedly attached to the housing 28 and therefore be stationary. The single moving jaw 26 would open and close to facilitate obtaining a sample.

FIG. 13 is a side view of an alternate jaw configuration. Moving around the jaw 120 clockwise beginning with the cutting edge 122, the configuration of the jaw 120 perimeter is as follows. Below the cutting edge 122, the edge is slightly indented. The indentation 124 provides a clean end to the cutting edge, thereby encouraging a clean cutting action. The indentation 124 also provides a transition between the cutting edge 122 and thicker portion of the jaw 120. Below the indentation 124 is an actuator engagement opening 126. The opening 126 is oblong with a convex-curved back wall 128, a rounded upper end 130, and a rounded lower end 132. An upper projection 134 extends down from the upper wall 130 of the opening 126, and a lower projection 136 extends up from the lower wall 132 of the opening 126. At the base 138 of each jaw 120 is a rounded portion 140. The rounded portion 140 touches the rounded portion 140 of the other jaw 120, thereby providing a smooth motion as the jaws 120 moved between the open and closed positions. Above the rounded portion 140 is a generally circular opening 142. The opening 142 is preferably greater than 180 degrees in circumference; as shown, it is approximately 250 degrees. The opening 142 provides a connection with the housing 28 by containing a generally cylindrical portion 70 of the housing 28. Preferably, the opposing side of the jaw 120 is shaped the same.

FIG. 14 is a side view of the instrument 20 showing three sections of coil forming the sheath 22 and a handle 150 having a spool 152 and thumb ring 154 for actuation of the jaws 26.

An alternate embodiment of the invention may have a rigid, semi-rigid, or articulated shaft. Other embodiments may have a malleable shaft, allowing the user to form the shaft into a desired shape prior to insertion into the body. In malleable embodiments, the channel within the sheath 22 which houses the control wire 24 must be of sufficient size to allow the sheath 22 to be in a bent configuration and have sufficient room for the control wire 24 to also be bent and still to move freely in the longitudinal direction. In these embodiments, it is preferable to use a solid control wire or rod 24 to provide additional stability when pushing the control wire 24 to open the jaws 26. Such embodiments would be useful for laparoscopic surgery.

Figure 16:
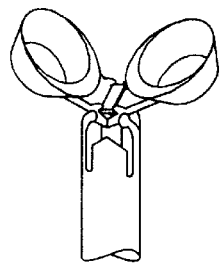
FIG. 16 is a biopsy forceps having round cup jaws.
Figure 17:
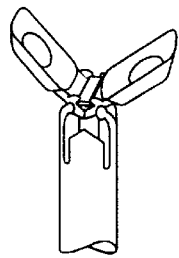
FIG. 17 is a biopsy forceps having short oval cup jaws.
Figure 18:
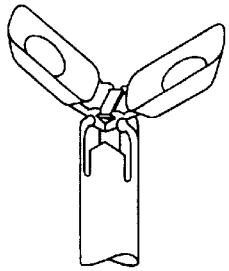
FIG. 18 is a biopsy forceps having long oval cup jaws.
Figure 19:
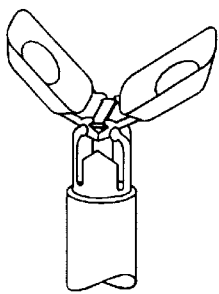
FIG. 19 is a hot biopsy forceps having long oval cup jaws.
Figure 20:
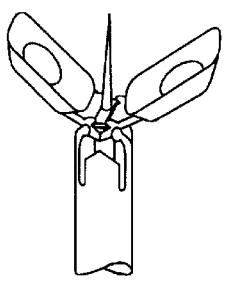
FIG. 20 is a biopsy forceps having long oval cup jaws and a spike.
Figure 21:
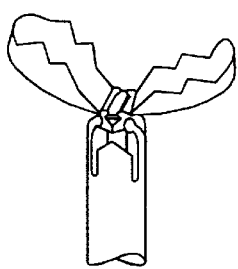
FIG. 21 is a biopsy forceps having long serrated jaws.
Figure 22:
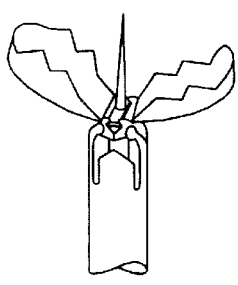
FIG. 22 is a biopsy forceps having long serrated jaws and a spike.
Figure 23:
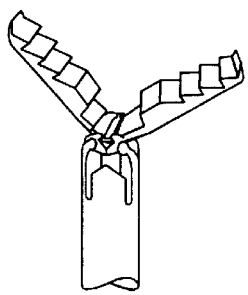
FIG. 23 is a grasping forceps having alligator jaws.
Figure 24:
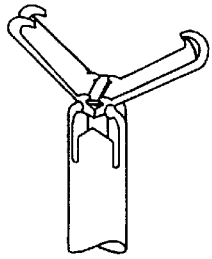
FIG. 24 is a grasping forceps having rat tooth jaws.

FIGS. 15–24 show several alternate embodiments using the actuation mechanism of the present invention. FIG. 15 is a side cross-sectional view of grasping forceps. FIG. 16 is a biopsy forceps having round cup jaws. FIG. 17 is a biopsy forceps having short oval cup jaws. FIG. 18 is a biopsy forceps having long oval cup jaws. FIG. 19 is a hot biopsy forceps having long oval cup jaws and having an electrical connection for cauterization. FIG. 20 is a biopsy forceps having long oval cup jaws and a spike. FIG. 21 is a biopsy forceps having long serrated jaws. FIG. 22 is a biopsy forceps having long serrated jaws and a spike. FIG. 23 is a grasping forceps having alligator jaws. FIG. 24 is a grasping forceps having rat tooth jaws.

The parts of the biopsy forceps 20 may be created by any conventional method including, but not limited to, conventional machining, turning, boring, grinding, electrical discharge machining, casting, molding such as injection, thermoform, etc. or combinations thereof.

Many features have been listed with particular configurations, options, and embodiments. Any one or more of the features described may be added to or combined with any of the other embodiments or other standard devices to create alternate combinations and embodiments.

Although the examples given include many specificities, they are intended as illustrative of only one possible embodiment of the invention. Other embodiments and modifications will, no doubt, occur to those skilled in the art. Thus, the examples given should only be interpreted as illustrations of some of the preferred embodiments of the invention, and the full scope of the invention should be determined by the appended claims and their legal equivalents.

What is claimed is:

1. An endoscopic instrument, comprising:
   a sheath having a proximal end and a distal end,
   a housing connected with said distal end of said outer sheath,
   a core wire having a proximal end and a distal end and passing through said sheath,
   a handle attached to said proximal end of said core wire,
   an actuation assembly attached to a distal end of said core wire and having a first projection,
   a first jaw having a first opening proximate a lower end thereof, said first jaw having a first position and a second position,
   and a second jaw,
   wherein said first projection is located at least partially within said first opening,
   wherein when said actuation assembly is moved longitudinally along a body of the instrument, said first jaw moves between the open position and the closed position.

2. The endoscopic instrument of claim 1 wherein said second jaw is stationary.

3. The endoscopic instrument of claim 1 further comprising a hole extending through at least one of said first jaw and said second jaw.

4. The endoscopic instrument of claim 1 further comprising a spike extending from a distal portion of said actuation assembly.

5. The endoscopic instrument of claim 1 wherein said first opening is an indentation in an edge of said first jaw.

6. The endoscopic instrument of claim 5 wherein said indentation is oblong with a convex-curved back wall, a rounded upper end, a rounded lower end, an upper projection extending down from said upper end, and a lower projection extending up from the lower end.

7. The endoscopic instrument of claim 1 wherein said first jaw has a triangular projection which extends downward from a base of said first jaw.

8. The endoscopic instrument of claim 1 wherein said first jaw has a rounded base.

9. The endoscopic instrument of claim 1 further comprising a pivot opening in said first jaw, said jaw being pivotable about said pivot opening.

10. The endoscopic instrument of claim 9 wherein said pivot opening is generally circular.

11. The endoscopic instrument of claim 9 wherein said pivot opening forms more than 180 degrees of a circle.

12. The endoscopic instrument of claim 1 wherein said first jaw is pivotally connected to said housing.

13. The endoscopic instrument of claim 1 wherein said first jaw has a cutting edge extending along an upper portion of said jaw.

14. The endoscopic instrument of claim 1 wherein a portion of said housing forms a pin around which said first jaw pivots.

15. The endoscopic instrument of claim 1 wherein said sheath is formed from at least three sections of coiled wire.

16. An endoscopic instrument, comprising:
an sheath having a proximal end and a distal end,
a housing connected with said distal end of said sheath,
a core wire having a proximal end and a distal end and passing through said sheath,
an actuation handle attached to said proximal end of said core wire,
a first jaw having a first opening and a second opening proximate a lower end thereof, said first jaw being connected with said housing at a first pivot point, said first jaw being pivotable about said first pivot point,
a second jaw having a third opening and a fourth opening proximate a lower end thereof, said second jaw being connected with said housing at a second pivot point, said second jaw being pivotable about said second pivot point,
and an actuation assembly connected with said distal end of said core wire and having a first projection and a second projection, said first projection being located at least partially within said first and third openings, said second projection being located at least partially within said second and fourth openings,
wherein when said actuation handle is moved, said actuation assembly moves longitudinally along said housing, thereby moving said first and second projections,
wherein when said first and second projections move, said first and second jaws move between an open position and a closed position.

17. The endoscopic instrument of claim 16 further comprising a hole extending through at least one of said first jaw and said second jaw.

18. The endoscopic instrument of claim 16 further comprising a spike extending from a distal portion of said actuation assembly.

19. The endoscopic instrument of claim 16 wherein said first and second openings are indentations in edges of said first jaw and said third and fourth openings are indentations in said second jaw.

20. The endoscopic instrument of claim 19 wherein said first opening, said second opening, said third opening and said fourth opening are each oblong with a convex-curved back wall, a rounded upper end, a rounded lower end, an upper projection extending down from said upper end, and a lower projection extending up from the lower end.

21. The endoscopic instrument of claim 16 wherein said first jaw has a cutting edge extending along an upper portion of said first jaw and said second jaw has a cutting edge extending along an upper portion of said second jaw.

22. The endoscopic instrument of claim 16 wherein said first jaw has a triangular projection which extends downward from a base of said first jaw and wherein said second jaw has a triangular projection which extends downward from a base of said second jaw.

23. The endoscopic instrument of claim 16 wherein said first jaw and said second jaw each have a rounded base.

24. The endoscopic instrument of claim 16 further comprising a first pivot opening in said first jaw and a second pivot opening in said second jaw, said first jaw being pivotable around said first pivot opening and said second jaw being pivotable around said second pivot opening.

25. The endoscopic instrument of claim 24 wherein said first and second pivot openings are generally circular.

26. The endoscopic instrument of claim 24 wherein said first and second pivot openings each form more than 180 degrees of a circle.

27. The endoscopic instrument of claim 16 said first jaw and said second jaw being pivotally connected to said housing.

28. The endoscopic instrument of claim 16 wherein a first portion of said housing forms a first pin around which said first jaw pivots and a second portion of said housing forms a second pin around which said second jaw pivots.

29. The endoscopic instrument of claim 16 further comprising at least one assembly opening in said housing, said at least one assembly opening forming a slot extending from a distal end thereof.

30. The endoscopic instrument of claim 16 further comprising a spike extending from a distal portion of said actuation assembly, wherein when said actuation assembly moves said jaws between said open and said closed position, said spike is moved longitudinally along said instrument towards the proximal end thereof, thereby urging any material in contact with said spike into a tissue opening created by said first and second jaws.

31. An endoscopic instrument, comprising:
an sheath having a proximal end and a distal end,
a generally rigid housing connected with said distal end of said sheath,
a core wire having a proximal end and a distal end and passing through said sheath,
an actuation handle attached to said proximal end of said core wire,
a first jaw having a first indentation and a second indentation proximate a lower end thereof, said first jaw being connected with said housing at a first pivot point, said first jaw being pivotable about said first pivot point, a first portion of said housing forming said first pivot point,
a second jaw having a third indentation and a fourth indentation proximate a lower end thereof, said second jaw being connected with said housing at a second pivot point, said second jaw being pivotable about said second pivot point, a second portion of said housing forming said second pivot pin,
and an actuation assembly connected with said distal end of said core wire and having a first projection and a second projection, said first projection being located at least partially within said first and third indentations, said second projection being located at least partially within said second and fourth indentations,
wherein when said actuation handle is moved, said actuation assembly moves longitudinally along said housing, thereby moving said first and second projections, wherein when said first and second projections move, said first and second jaws move between an open position and a closed position.

32. The endoscopic instrument of claim 31 further comprising at least one assembly opening in said housing, said at least one assembly opening forming a slot extending from a distal end thereof.

33. The endoscopic instrument of claim 31 further comprising a spike extending from a distal portion of said actuation assembly, wherein when said actuation assembly moves said jaws between said open and said closed position, said spike in moved longitudinally along said instrument, thereby urging any material in contact with said spike into a tissue opening created by said first and second jaws.

* * * * *